United States Patent [19]

Gold et al.

[11] Patent Number: 4,929,552
[45] Date of Patent: May 29, 1990

[54] CHEMICAL AND ENZYMATIC PROCESS FOR THE DENITRATION OF DIETHYLENEGLYCOL DINITRATE, NITROGLYCERIN AND OTHER NITRATE ESTERS

[75] Inventors: Kenneth Gold, Hastings-On-Hudson, N.Y.; Bruce Brodman, Stroudsburg, Pa.

[73] Assignee: The United States of America as represented by the Secretary of the Army, Washington, D.C.

[21] Appl. No.: 438,955

[22] Filed: Nov. 17, 1989

Related U.S. Application Data

[63] Continuation of Ser. No. 87,942, Aug. 17, 1987, abandoned.

[51] Int. Cl.$^5$ .............................................. C12P 13/00
[52] U.S. Cl. ..................................................... 435/128
[58] Field of Search ........................................... 435/128

[56] References Cited

U.S. PATENT DOCUMENTS

| | | | |
|---|---|---|---|
| 4,250,267 | 2/1981 | Hartdegen et al. | 435/317.1 |
| 4,764,368 | 8/1988 | Blattler et al. | 435/177 |
| 4,764,467 | 8/1988 | Goertz et al. | 435/180 |

*Primary Examiner*—Ronald W. Griffin
*Assistant Examiner*—Pamela S. Webber
*Attorney, Agent, or Firm*—Robert P. Gibson; Edward Goldberg; Edward F. Costigan

[57] ABSTRACT

A process for denitrating the dinitrate ester of diethyleneglycol is disclosed which comprises introducing the dinitrate ester of diethyleneglycol into an aqueous phosphate buffer containing the tripeptide reduced glutathione and the enzyme glutathione S-transferase.

5 Claims, No Drawings

CHEMICAL AND ENZYMATIC PROCESS FOR THE DENITRATION OF DIETHYLENEGLYCOL DINITRATE, NITROGLYCERIN AND OTHER NITRATE ESTERS

STATEMENT OF GOVERNMENT INTEREST

The invention described herein may be manufactured, used and licensed by or for the Government without the payment of any royalties thereon.

This application is a continuation of application Ser. No. 07/087,942, filed Aug. 17, 1987, now abandoned.

The invention described herein may be manufactured, used and licensed by or for the Government without the payment of any royalties thereon.

FIELD OF INVENTION

In general, this invention relates to the degradation of diethyleneglycol dinitrate otherwise known as the dinitrate ester of diethyleneglycol.

More particularly, this invention relates to an improved process for use in the denitration of diethyleneglycol dinitrate, nitroglycerin, and related nitrate esters.

BACKGROUND OF INVENTION

The process of the present invention solves the problem of disposal of scrap diethyleneglycol dinitrate (DEGDN), nitroglycerin (NG) and related nitrate esters, produced during manufacture and demilitarization of propellants and explosives. The problem has existed since propellants and explosives were first manufactured for use in ammunition or for demolition purposes.

The disposal of propellant and explosive scrap material has been dealt with in the past by burning, exploding the scrap material in air, or by chemical degradation such as alkaline hydrolysis. Ignition is dangerous and results in air pollution, and such methods are illegal in many locations.

Also, digestion by hydrolysis requires the application of strong caustic solutions, and the products of this digestion may lead to pollution of streams and groundwater. In the art there are also processes designed for the degradation of such materials as nitrocellulose which is a related material. In one such process, nitrocellulose is subjected to alkaline hydrolysis followed by microbial digestion of the products.

A safety advantage of the process of the present invention is avoidance of strong alkali. In addition, in the cited process of the art, the microbial populations may be variable unless carefully controlled which may be difficult. However, in the process of the present invention, treatment with enzymes can be very easily controlled and adjusted at will. The use of enzymes as provided by this invention, simplifies the denitration process and avoids some of the disposal problems associated with inorganic nitrogencontaining waste products.

It is an object of this invention to provide an improved process for use in the denitration of diethyleneglycol dinitrate, nitroglycerin, and related nitrate esters.

Another object is to provide an improved process which is more effective and efficient in use for the dinitration of diethyleneglycol dinitrate without the difficulties encountered in the art for similar processes.

A further object of this invention is to provide a process of dinitrating diethyleneglycol dinitrate which is safe and facile in use under an acceptable range of operating conditions in a laboratory or plant.

Other objects and many of the attendant advantages of the process of the present invention will become obvious to those skilled in the art from a reading of the following detailed specifications.

SUMMARY OF THE INVENTION

The process of this invention provides a nucleophilic attack on the nitrate ester groups of the diethyleneglycol dinitrate by the tripeptide reduced glutathione with a 2-3 fold enhancement of the process by the enzyme glutathione S-transferase which acts as a catalyst. This process is not only applicable to diethyleneglycol dinitrate. Nitroglycerin, nitrated sugars, and related energetic substances may also be treated in the same manner with similar results.

PREFERRED EMBODIMENT

In the initial phase of the process, (0.3 mM) of tripeptide reduced glutathione was added to (1 ml) of an aqueous phosphate buffer containing (0.1 mg) of the enzyme glutathione S-transferase. The pH of the buffered solution was about 7.6. The glutathione chemical is active at low concentration between about 0.03 mM and about 1.8 mM. However, the optimum concentration was found to be about 0.3 mM at 25 C. At this point, 5 microliters of diethyleneglycol dinitrate was added to the cited mixture, and this started the reaction. It was found that the release of nitrate ions from the diethyleneglycol dinitrate by the cited chemical was about 10-fold the amount produced by the alkaline hydrolysis of DEGDN caused by the buffer alone.

It was found that the described enzyme enhanced the denitration of the diethyleneglycol dinitrate by reduced glutathione by at least a factor of 2 to 3. It was also found that more effective enhancement could be achieved by optimization of the enzyme and the substrate concentration, viz. the diethyleneglycol dinitrate. The enzyme utilized in the above procedure was obtained commercially as rabbit liver glutathione s-transferase which is about 75 percent protein. This was employed at a concentration of 0.1 mg/ml. This enzyme, when obtained from other sources such as tissues from various mammalian species, will also produce the desired enhancement of the denitration procedure.

The chemical reduced glutathione, which is -L-Glutamyl-L-Cysteinylglycine, and the glutathione S-transferase enzyme were both obtained commerically from Sigma Chemical Company, St. Louis, Mo.

The glutathione chemical may be present in the reaction mixture between about 0.03 mM and about 1.8 mM, but preferably about 0.3 mM. Also, the cited enzyme may be present in the range of between about 0.05 mg/ml and about 0.3 mg/ml. However, 0.1 mg/ml is the preferred amount of enzyme utilized in the experiments.

Further, the pH of the buffered solution was found effective for denitration between about 7 and about 8. Also, the temperature of the reaction in all cases was between about 25° C. and about 30° C.

In practice, the glutathione chemical and the enzyme are both added to the potassium phosphate buffer which contains sodium ethylenediaminetetraacetic acid (2 mM), and the reaction is initiated by the addition of the diethyleneglycol dinitrate in an amount of 5 microliters per ml of buffer. Periodic agitation is utilized to break up the diethyleneglycol dinitrate into small droplets for a more effective denitration reaction.

There are other laboratory procedures which may be used to enhance the denitration such as adding an emulsifier to the buffer solution. If the energetic material is emulsified, the surface area of the material exposed to the enzyme and glutathione chemical is increased for a more effective denitration. Further, glutathione reductase and the cofactor reduced nicotinamide adenine dinucleotide phosphate may be added to the reaction mixture to reduce the oxidized glutathione as it is produced. Thus, as the glutathine is oxidized, it is reduced enzymatically in the same reaction vessel. Still further, the specific activity of the enzyme may be increased by further purification.

In conclusion, the present process for the denitration of nitrate esters offers all of the advantages associated with the enzymatic modification of substrates. These advantages include speed of the reaction, relatively low cost of the materials involved and their commerical availability, relative safety in handling of the energetic subtrates and the products of the reaction. The present process is inherently safer than ignition of nitrate esters in air, and the process of the present invention eliminates safety problems associated with the operations or processes of the art which are carried out at high pH. Moreover, some of the reagents are recyclable which may lead to meaningful cost savings. For instance, cost savings can be achieved by reutilization of the enzyme and by recovery and recycling of glutathione.

What is claimed is:

1. An improved process of denitrating the dinitrate ester of diethyleneglycol comprising introducing the dinitrate ester of diethyleneglycol into an aqueous phosphate buffer containing the tripeptide reduced glutathione and the enzyme glutathione S-transferase.

2. The process of claim 1 wherein said dinitrate ester of diethyleneglycol is present in an amount between about 1 microliter and about 10 microliters, said buffer is present in an amount between about 0.5 ml and about 2.0 ml, said tripeptide reduced glutathione is present in an amount between about 0.3 and about 1.8 mM, and said glutathione S-transferase 0.3 mg/ml.

3. The process of claim 2 wherein 5 microliters of said dinitrate ester of diethyleneglycol is introduced into 1 ml of said aqueous phosphate buffer containing 0.3 mM of said tripeptide reduced glutathione and 0.1 mg of said glutathione S-transferase.

4. The process of claim 3 wherein said phosphate buffer is maintained at a pH between about 7.0 and about 8.0.

5. The process of claim 4 wherein the temperature is maintained between about 22 C. and about 37 C.

* * * * *